(12) United States Patent  (10) Patent No.: US 6,992,101 B2
Bussolotti et al.  (45) Date of Patent: Jan. 31, 2006

(54) N-(INDOLE-2-CARBONYL) AND H-THIENO[2,3-B]PYRROLE-5-CARBOXAMIDE ANTI-DIABETIC AGENTS

(75) Inventors: Donald L. Bussolotti, Ledyard, CT (US); Ronald B. Gammill, Schoolcraft, MI (US); Jana Polivkova, Ledyard, CT (US)

(73) Assignee: Pfizer, Inc., New York, NY (US)

( * ) Notice: Subject to any disclaimer, the term of this patent is extended or adjusted under 35 U.S.C. 154(b) by 139 days.

(21) Appl. No.: 10/703,035

(22) Filed: Nov. 6, 2003

(65) Prior Publication Data

US 2004/0157907 A1  Aug. 12, 2004

Related U.S. Application Data

(60) Provisional application No. 60/424,627, filed on Nov. 7, 2002.

(51) Int. Cl.
  C07D 209/04  (2006.01)
  C07D 495/02  (2006.01)
  A61K 31/407  (2006.01)
  A61K 31/381  (2006.01)

(52) U.S. Cl. .................. 514/412; 514/428; 514/430; 514/432; 514/446; 548/452; 548/453; 549/13; 549/70; 549/83; 549/88

(58) Field of Classification Search .......... 514/412, 514/428, 430, 432, 446; 548/453, 452; 549/13, 549/70, 83, 88
See application file for complete search history.

(56) References Cited

U.S. PATENT DOCUMENTS 6,576,653 B2 *  6/2003  Du Bois ................ 514/414

FOREIGN PATENT DOCUMENTS

| EP | 1340500 | 9/2003 |
|---|---|---|
| EP | 1088824 | 1/2004 |
| WO | WO 9639384 | 12/1996 |
| WO | WO 9639385 | 12/1996 |
| WO | WO 0220530 | 3/2002 |
| WO | WO 03074484 | 9/2003 |

* cited by examiner

*Primary Examiner*—Taofiq Solola
*Assistant Examiner*—Susannah E. Lee
(74) *Attorney, Agent, or Firm*—Gregg C. Benson; Carl J. Goddard

(57) ABSTRACT

The present invention provides compounds of formula (I)

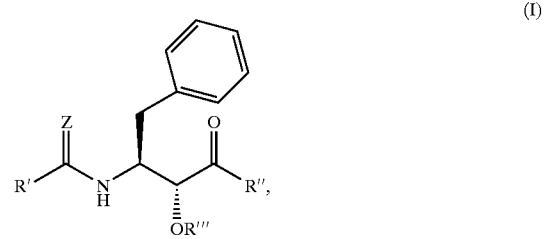

(I)

the prodrugs thereof, and the pharmaceutically acceptable salts of the compounds and prodrugs, wherein R', R", R''', and Z are as defined herein; pharmaceutical compositions thereof; and uses thereof in treating diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia.

11 Claims, No Drawings

N-(INDOLE-2-CARBONYL) AND H-THIENO[2,3-B]PYRROLE-5-CARBOXAMIDE ANTI-DIABETIC AGENTS

CROSS REFERENCE TO RELATED APPLICATION

This application claims the benefit of U.S. Provisional Application No. 60/424,627 filed Nov. 7, 2002.

BACKGROUND OF THE INVENTION

The invention relates to certain substituted N-(indole-2-carbonyl)amides and 6H-thieno[2,3-b]pyrrole-5-carboxamides which are antidiabetic agents and, as such, are useful in the treatment of diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia, particularly myocardial ischemia. This invention also relates to methods of using such compounds in the treatment of the above diseases in mammals, especially humans, and to pharmaceutical compositions useful therefor.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatment of diabetes remains less than satisfactory.

The use of insulin requires multiple daily doses, usually by self-injection. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can either have side effects limiting their use, or an agent may not be effective with a particular patient. In the case of insulin dependent diabetes mellitus (Type I), insulin administration usually constitutes the primary course of therapy. Hypoglycemic agents that have fewer side effects or succeed where others fail are needed.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque," which consists of accumulated intimal smooth muscle cells laden with lipid and surrounded by extra-cellular lipid, collagen, elastin and proteoglycans. The cells plus matrix form a fibrous cap that covers a deeper deposit of cell debris and more extra cellular lipid. The lipid is primarily free and esterified cholesterol. The fibrous plaque forms slowly, and is likely in time to become calcified and necrotic, advancing to the so-called "complicated lesion", which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, medical professionals have placed renewed emphasis on lowering plasma cholesterol levels, and low-density lipoprotein cholesterol in particular, as an essential step in prevention of CVD. The upper limits of "normal" are now known to be significantly lower than heretofore appreciated. As a result, large segments of Western populations are now realized to be at particularly high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (high blood pressure) is a condition that occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been fully elucidated. Additionally, many patients present with symptoms of high blood pressure in the complete absence of any other signs of disease or disorder.

It is known that hypertension can directly lead to heart failure, renal failure and stroke (brain hemorrhaging). These conditions are capable of causing death in a patient. Hypertension can also contribute to the development of atherosclerosis and coronary disease. These conditions gradually weaken a patient and can lead to death.

The exact etiology of "essential" hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels, and genetic disposition.

The treatment of "essential" hypertension has been undertaken bearing the foregoing factors in mind. Thus, a broad range of beta-blockers, vasoconstrictors, angiotensin-converting enzyme (ACE) inhibitors, and the like have been developed and marketed as antihypertensives. The treatment of hypertension utilizing these compounds has proven beneficial in the prevention of short-interval deaths such as heart failure, renal failure, and brain hemorrhaging. However, the development of atherosclerosis or heart disease due to hypertension over a long period of time remains problematic. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis, and the formation and storage of neutral lipids, also acts, inter alia, to promote vascular cell growth and increase renal sodium retention. These latter functions can be accomplished without affecting glucose levels and are known causes of hypertension. Peripheral vasculature growth, for example, can cause constriction of peripheral capillaries while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion that can occur in both outpatient and perioperative settings. There is currently an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no marketed drug therapy in this area that reduces damage to cardiac tissue from perioperative myocardial ischemia or enhances cardiac resistance to ischemic episodes. Such a therapy is anticipated to be life-saving, reduce hospitalizations, enhance quality of life, and reduce overall health care costs of high-risk patients. The mechanism(s) responsible for the myocardial injury observed after ischemia and reperfusion is not fully understood, however, it has been reported (M. F. Allard, et al., Am. J. Physiol., 267: H66–H74 (1994)) that "pre-ischemic glycogen reduction . . . is associated with improved post-ischemic left ventricular functional recovery in hypertrophied rat hearts."

In addition to myocardial ischemia, other tissues can undergo ischemia and be damaged resulting in serious problems for the patient. Examples of such tissues include cardiac, brain, liver, kidney, lung, gut, skeletal muscle, spleen, pancreas, nerve, spinal cord, retina tissue, the vasculature, or intestinal tissue.

Hepatic glucose production is an important target for NIDDM therapy. The liver is the major regulator of plasma glucose levels in the post absorptive (fasted) state, and the rate of hepatic glucose production in NIDDM patients is significantly elevated relative to normal individuals. Likewise, in the postprandial (fed) state, where the liver plays a proportionately smaller role in the total plasma glucose supply, hepatic glucose production is abnormally high in NIDDM patients.

Glycogenolysis is an important target for interruption of hepatic glucose production. The liver produces glucose by glycogenolysis (breakdown of the glucose polymer glycogen) and gluconeogenesis (synthesis of glucose from 2- and 3-carbon precursors). Several lines of evidence indicate that glycogenolysis may make an important contribution to hepatic glucose output in NIDDM. First, in normal post absorptive man, up to 75% of hepatic glucose production is estimated to result from glycogenolysis. Second, patients having liver glycogen storage diseases, including Hers' disease (glycogen phosphorylase deficiency), display episodic hypoglycemia. These observations suggest that glycogenolysis may be a significant process for hepatic glucose production.

Glycogenolysis is catalyzed in liver, muscle, and brain by tissue-specific isoforms of the enzyme glycogen phosphorylase. This enzyme cleaves the glycogen macromolecule to release glucose-1-phosphate and a new shortened glycogen macromolecule. Several types of glycogen phosphorylase inhibitors have been reported to date: glucose and glucose analogs [J. L. Martin, et al., Biochemistry, 30:10101 (1991)]; caffeine and other purine analogs [P. J. Kasvinsky, et al., J. Biol. Chem., 253: 3343–3351 and 9102–9106 (1978)]; substituted N-(indole-2-carbonyl)-amides [PCT Publication Number WO 96/39385]; and substituted N-(indole-2-carbonyl)-glycinamides [PCT Publication Number WO 96/39384]. These compounds, and glycogen phosphorylase inhibitors in general, have been postulated to be of use for the treatment of NIDDM by decreasing hepatic glucose production and lowering glycemia. [T. B. Blundell, et al., Diabetologia, 35: Suppl. 2, 569–576 (1992) and Martin et al., Biochemistry, 30: 10101 (1991)].

Myocardial ischemic injury can occur in outpatient as well as in perioperative settings and can lead to the development of sudden death, myocardial infarction, or congestive heart failure. There is currently an unmet medical need to prevent or minimize myocardial ischemic injury, particularly perioperative myocardial infarction. Such a therapy is anticipated to be life-saving, reduce hospitalizations, enhance quality of life, and reduce overall health care costs of high-risk patients. Although there are a variety of hyperglycemia, hypercholesterolemia, hypertension, hyperlipidemia, atherosclerosis and tissue ischemia therapies, there is a continuing need in the art for alternative therapies.

SUMMARY OF THE INVENTION

The present invention provides compounds of formula (I)

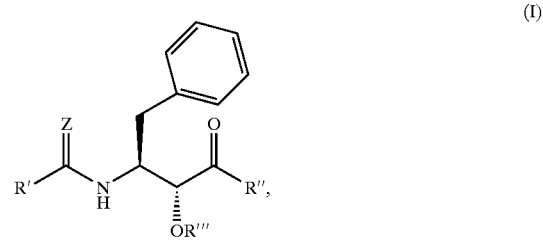

(I)

the prodrugs thereof, and the pharmaceutically acceptable salts of the compounds and prodrugs, wherein R', R", R''', and Z are as defined herein; pharmaceutical compositions thereof; and uses thereof in treating diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, and tissue ischemia.

DETAILED DESCRIPTION OF THE INVENTION

The present invention provides compounds of formula (I)

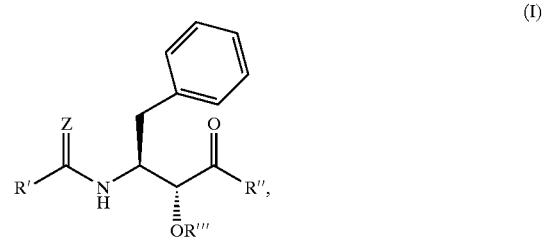

(I)

the prodrugs thereof, and the pharmaceutically acceptable salts of the compounds and prodrugs, wherein:

R' is

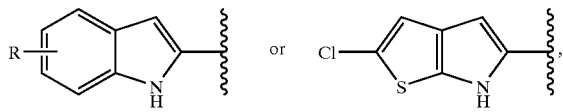 or 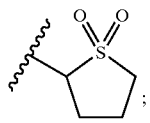

wherein R represents from 1–3 substituents independently selected from the group consisting of hydrogen; amino; cyano; nitro; halogen; —(C$_1$–C$_6$)alkyl; and —(C$_1$–C$_6$)alkoxy, wherein the —(C$_1$–C$_6$)alkyl group and the —(C$_1$–C$_6$)alkoxy group are each optionally substituted with from 1–6 fluorine atoms;

R" is (i)

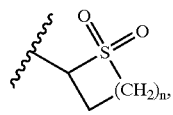

wherein n represents an integer from 1–3; or (ii) —CHR$^a$SO$_2$(C$_1$–C$_6$)alkyl, wherein R$^a$ is hydrogen or —(C$_1$–C$_6$)alkyl;

R'" is hydrogen or —(C$_1$–C$_6$)alkyl; and

Z is oxygen or sulfur.

A generally preferred subgroup of the compounds of formula (I) comprises those compounds wherein:

R' is

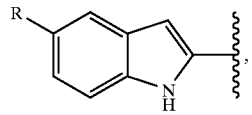

wherein R is selected from the group consisting of chloro, fluoro, and methyl;

R" is

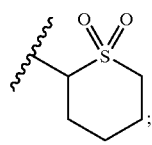

R'" is hydrogen or methyl; and

Z is oxygen.

Another generally preferred subgroup of the compounds of formula (I) comprises those compounds wherein:

R' is

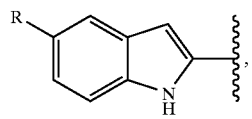

wherein R is selected from the group consisting of chloro, fluoro, and methyl;

R" is

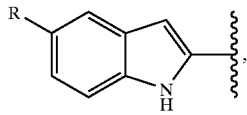

R'" is hydrogen or methyl; and

Z is oxygen.

Another generally preferred subgroup of the compounds of formula (I) comprises those compounds wherein:

R' is

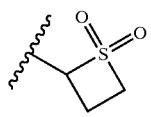

wherein R is selected from the group consisting of chloro, fluoro, and methyl;

R" is

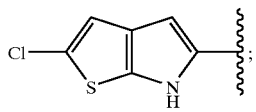

R'" is hydrogen; and

Z is oxygen.

Yet another generally preferred subgroup of the compounds of formula (I) comprises those compounds wherein:

R' is

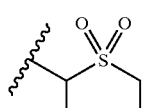

R" is

R'" is methyl; and

Z is oxygen.

Yet another generally preferred subgroup of the compounds of formula (I) comprises those compounds wherein:

R' is

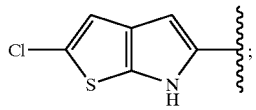

R" is

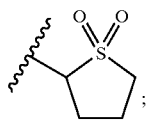

R'" is hydrogen or methyl; and

Z is oxygen.

An especially preferred subgroup of the compounds of formula (I) comprises those compounds selected from the group consisting of:

5-chloro-1H-indole-2-carboxylic acid-(1-benzyl-3-(1,1-dioxo-tetrahydro-1-thiophen-2-yl)-2-hydroxy-3-oxo-propyl]-amide;

5-chloro-1H-indole-2-carboxylic acid-(1-benzyl-3-(1,1-dioxo-1-tetrahydro-1-thiophen-2-yl)-2-methoxy-3-oxo-propyl]-amide;

5-chloro-1H-indole-2-carboxylic acid-[1-benzyl-3-(1,1-dioxo-hexahydro-1-thiopyran-2-yl)-2-methoxy-3-oxo-propyl]-amide;

5-chloro-1H-indole-2-carboxylic acid-[1-benzyl-3-(1,1-dioxo-hexahydro-1-thiopyran-2-yl)-2-hydroxy-3-oxo-propyl]-amide;

2-chloro-6H-thieno[2,3-b]pyrrole-5-carboxylic acid-[1-benzyl-3-(1,1-dioxo-tetrahydro-1-thiophen-2-yl)-2-hydroxy-3-oxo-propyl]-amide;

2-chloro-6H-thieno[2,3-b]pyrrole-5-carboxylic acid-[1-benzyl-3-(1,1-dioxo-tetrahydro-1-thiophen-2-yl)-2-methoxy-3-oxo-propyl]-amide; and 2-chloro-6H-thieno[2,3-b]pyrrole-5-carboxylic acid-[1-benzyl-3-(1,1-dioxo-hexahydro-1-thiopyran-2-yl)-2-methoxy-3-oxo-propyl]-amide; the prodrug thereof, and the pharmaceutically acceptable salts of the compounds and prodrugs.

The compounds and intermediates of the present invention may be named according to either the IUPAC (International Union for Pure and Applied Chemistry) or CAS (Chemical Abstracts Service, Columbus, Ohio) nomenclature systems.

The carbon atom content of the various hydrocarbon-containing moieties herein may be indicated by a prefix designating the minimum and maximum number of carbon atoms in the moiety, for example, the prefix $(C_a-C_b)$alkyl indicates an alkyl moiety of the integer "a" to "b" carbon atoms, inclusive. Thus, for example, $(C_1-C_6)$alkyl refers to an alkyl group of one to six carbon atoms inclusive, for example, methyl, ethyl, propyl, isopropyl, butyl, isobutyl, pentyl, isopentyl, hexyl, and the like, including all regioisomeric forms thereof, and straight and branched chain forms thereof.

The term "alkoxy" refers refers to straight or branched, monovalent, saturated aliphatic chains of carbon atoms bonded to an oxygen atom. Examples of alkoxy groups include methoxy, ethoxy, propoxy, butoxy, iso-butoxy, tert-butoxy, pentoxy, and the like.

The term "alkyl" refers to straight or branched, monovalent, saturated aliphatic chains of carbon atoms and includes, for example, methyl, ethyl, propyl, isopropyl, butyl, isobutyl, pentyl, isopentyl, hexyl, and the like.

The term "halogen" represents chloro, fluoro, bromo, and iodo.

The term "mammal" means animals including, for example, dogs, cats, cows, sheep, horses, and humans. Preferred mammals include humans.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug precursor which, following administration, releases the drug in vivo via a chemical or physiological process (e.g., upon being brought to physiological pH or through enzyme activity). A discussion of the synthesis and use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "radical" denotes a group of atoms that behaves as a single atom in a chemical reaction, e. g., an organic radical is a group of atoms that imparts characteristic properties to a compound containing it, or which remains unchanged during a series of reactions, or transformations.

The term "salts" refers to organic and inorganic salts of a compound of formula (I), or a stereoisomer, or prodrug thereof. These salts can be prepared in situ during the final isolation and purification of a compound, or by separately reacting a compound of formula (I), or a stereoisomer or prodrug thereof, with a suitable organic or inorganic acid or base and isolating the salt thus formed. Representative salts include the hydrobromide, hydrochloride, sulfate, bisulfate, nitrate, acetate, oxalate, besylate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, as the like. These may also include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. For additional examples see, for example, Berge, et al., J. Pharm. Sci., 66, 1–19 (1977).

The term "substituted" means that a hydrogen atom on a molecule has been replaced with a different atom or molecule. The atom or molecule replacing the hydrogen atom is denoted as a "substituent."

The symbol "—" represents a covalent bond.

The phrase "reaction-inert solvent" or "inert solvent" refers to a solvent, or mixture of solvents, that does not interact with starting materials, reagents, intermediates, or products in a manner that adversely affects their desired properties. The terms "treating", "treated", or "treatment" as employed herein includes preventative (e.g., prophylactic), palliative, or curative use or result.

The terms "treating", "treated", or "treatment" as employed herein includes preventative (e.g., prophylactic), palliative, or curative use or result.

The compounds of formula (I) may contain asymmetric or chiral centers and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. For example, if a compound of formula (I) incorporates a double bond, both the cis- and trans- forms, as well as mixtures thereof, are embraced within the scope of the invention.

Diasteriomeric mixtures can be separated into their individual diastereomers on the basis of their physical chemical differences by methods well-known to those of ordinary skill in the art, such as by chromatography and/or fractional crystallization. Enantiomers can be separated by converting the enantiomeric mixture into a diasteriomeric mixture by reaction with an appropriate optically active compound (e.g., alcohol), separating the diasteriomers and converting (e.g., hydrolyzing) the individual diasteriomers to the corresponding pure enantiomers. Also, some of the compounds of formula (I) may be atropisomers (e.g., substituted biaryls) and are also considered as part of the invention.

The compounds of formula (I) may exist in unsolvated as well as solvated forms with pharmaceutically acceptable solvents, such as water, ethanol, and the like, and it is intended that the invention embrace both solvated and unsolvated forms.

It is also possible that the compounds of formula (I) may exist as tautomeric isomers in equilibrium, and all such forms are embraced within the scope of the invention.

The present invention also embraces isotopically-labeled compounds of formula (I), which are identical to those recited herein, but for the fact that one or more atoms are replaced by an atom having an atomic mass or mass number different from the atomic mass or mass number usually found in nature. Examples of isotopes that can be incorporated into compounds of formula (I) include isotopes of hydrogen, carbon, nitrogen, oxygen, phosphorus, fluorine, and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. The compounds of formula (I), the stereoisomers and prodrugs thereof, and the pharmaceutically acceptable salts of the compounds, stereoisomers, or prodrugs, that contain the aforementioned isotopes and/or other isotopes of the other atoms are intended to be within the scope of the instant invention.

Certain isotopically-labeled compounds of formula (I), for example those compounds into which radioactive isotopes such as $^3$H and $^{14}$C are incorporated, are useful in compound and/or substrate tissue distribution assays. Tritiated, i.e., $^3$H, and carbon-14, i.e., $^{14}$C, isotopes are particularly preferred for their relative ease of preparation and facile detection. Furthermore, substitution with heavier isotopes such as deuterium, i.e., $^2$H, may afford certain therapeutic advantages resulting from greater metabolic stability, for example, increased in vivo half-life, or reduced dosage requirements and, hence, may be preferred in some circumstances. The isotopically-labeled compounds of formula (I) can generally be prepared by carrying out procedures analogous to those disclosed in the Schemes and/or Examples set forth hereinbelow, by substituting an isotopically-labeled reagent for a non-isotopically-labeled reagent.

In another aspect, the invention provides methods of treating conditions selected from the group consisting of atherosclerosis, diabetes, insulin resistance, diabetic neuropathy, diabetic nephropathy, diabetic retinopathy, cataracts, hypercholesterolemia, hypertriglyceridemia, hyperlipidemia, hyperglycemia, hypertension, and tissue ischemia, including mycardial ischemia, which comprise administering to a mammal in need of such treatment, a therapeutically effective amount of a compound of formula (I), a prodrug thereof, or a pharmaceutically acceptable salt of the compound or prodrug; or a pharmaceutical composition comprising a compound of formula (I), or a prodrug thereof, or a pharmaceutically acceptable salt of the compound or prodrug, and a pharmaceutically acceptable carrier, vehicle, or diluent. A preferred condition comprises diabetes.

In another aspect, the invention provides methods for inhibiting glycogen phosphorylase which comprises administering to a mammal in need of such inhibition, a glycogen phosphorylase inhibiting amount of a compound of formula (I), a prodrug thereof, or a pharmaceutically acceptable salt of the compound or prodrug; or a pharmaceutical composition comprising a compound of formula (I), or a prodrug thereof, or a pharmaceutically acceptable salt of the compound or prodrug, and a pharmaceutically acceptable carrier, vehicle, or diluent.

The compounds of formula (I) may be administered to a mammal at dosage levels in the range of from about 0.1 mg to about 3,000 mg per day. For a normal adult human having a body mass of about 70 kg, a dosage in the range of from about 0.01 mg to about 100 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular mammalian subject is within the ability of one of ordinary skill in the art having benefit of the instant disclosure.

According to the methods of the present invention, a compound of formula (I), a prodrug thereof, or a pharmaceutically acceptable salt of the compound or prodrug, may be administered in the form of a pharmaceutical composition comprising a pharmaceutically acceptable carrier, vehicle, or diluent. Accordingly, a compound of formula (I), a prodrug thereof, or a pharmaceutically acceptable salt of the compound or prodrug, may be administered to a subject separately or together in any conventional oral, rectal, transdermal, parenteral (e.g., intravenous, intramuscular, or subcutaneous), intracisternal, intravaginal, intraperitoneal, intravesical, local (e.g., powder, ointment, or drop), or buccal, or nasal dosage form.

Pharmaceutical compositions suitable for parenteral injection may comprise pharmaceutically acceptable sterile aqueous or nonaqueous solutions, dispersions, suspensions, or emulsions, and sterile powders for extemporaneous reconstitution into sterile injectable solutions or dispersions. Examples of suitable aqueous and nonaqueous carriers, vehicles, and diluents include water, ethanol, polyols (such as propylene glycol, polyethylene glycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions, and by the use of surfactants.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like.

Prolonged absorption of of injectable pharmaceutical compositions may be effected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound(s) in a delayed, sustained, or controlled manner. Examples of embedding compositions that can be employed are polymeric substances and waxes. The active compound(s) can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound(s), may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing an active compound(s) with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent(s) are admixed under sterile condition with a pharmaceutically acceptable carrier, vehicle, or diluent, and any preservatives, buffers, or propellants that may be required.

The compounds of formula (I) may be prepared according to the exemplary synthetic route disclosed in Scheme I hereinbelow, as well as by other conventional organic preparative methods. It is to be understood that the method disclosed in Scheme 1 is intended for purposes of exemplifying the instant invention, and is not to be construed in any manner as a limitation thereon.

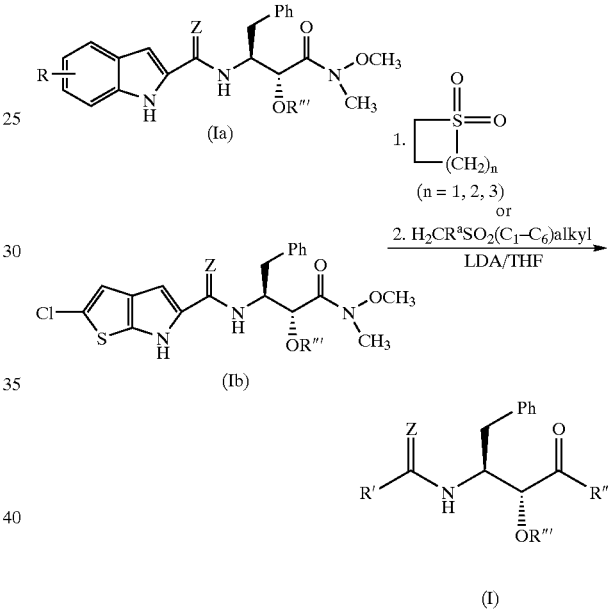

In Scheme 1 hereinabove, an appropriately-substituted 1H-indole-2-carboxylic acid derivative (Ia) or 6-chloro-6H-thieno[2,3-b]pyrrole-5-carboxylic acid derivative (Ib) is coupled with: (1) trimethylene sulfone (prepared as described in Synthesis, 7, 582–583 (1982)), tetrahydrothiophene-1,1-dioxide (sulfolane), or tetrahydro-1,1-dioxide-2H-thiopyran (prepared as described in J. Am. Chem. Soc., 114, 3021 (1992)), or (2) an acylic sulfone auxiliary of structural formula $H_2CR^aSO_2(C_1-C_6)$alkyl, wherein $R^a$ is hydrogen or —$(C_1-C_6)$alkyl to afford (I). The coupling is typically effected in an aprotic, non-polar solvent, such as ether or tetrahydrofuran, in the presence of a strong organic base, such as lithium diisopropylamide. The coupling is normally effected below ambient temperature, preferably at, or about, −78° C.

The substituted indole derivatives of general structure (Ia) may be prepared according to the methods disclosed in commonly-assigned U.S. Pat. No. 6,297,269, the disclosure of which is incorporated herein by reference. The compounds of general structure (Ib) may be prepared as described hereinbelow in exemplary Preparation 1 or, alternatively, according to the methodologies disclosed in commonly-assigned U.S. Pat. No. 6,399,601, the disclosure of which is incorporated herein by reference.

Preparative Experimental

Unless otherwise noted, all reactants and reagents were obtained commercially. Unless indicated otherwise, the following experimental abbreviations have the indicated meanings:

DMF—N,N-dimethylformamide
HOBT—hydroxybenzotriazole hydrate
HPLC—high performance liquid chromatography
hr(s)—hour(s)
LC/MS—liquid chromatography/mass spectrometry
min(s)—minute(s)
THF—tetrahydrofuran

PREPARATION 1

2-Chloro-6H-thieno[2,3-b]pyrrole-5-carboxylic acid-[1-benzyl-2-methoxy-2-(methoxymethyl-carbamoyl)-ethyl]-amide (1b, Z=O, R'''=CH$_3$)

Triethylamine was added dropwise to a solution of 3-amino-2,N-dimethoxy-N-methyl-4-phenyl-butyramide (PCT International Application Publication No. WO 96/39385) (1.65 g, 5.71 mmol) in DMF (15 mL) and cooled in an ice bath. A solution of 2-chloro-6H-thieno[2,3-b] pyrrole-5-carboxylic acid (U.S. Pat. No. 6,399,601) (1.1 g, 5.71 mmol) in 15 mL of DMF was added dropwise followed by the addition of HOBT (1.16 g, 11.4 mmol) neat. The reaction mixture was stirred for 5 min and N-ethyliminomethylene-N,N'-dimethyl-propane-1,3-diamine (1.10 g, 5.71 mmol) was added neat. The resulting mixture was stirred at room temperature for 18 hrs. The reaction mixture was diluted with ethyl acetate (150 mL) and washed with saturated ammonium chloride, water, and brine. The ethyl acetate was dried and evaporated in vacuo to yield 2.54 g of crude product. Chromatography over silica gel, eluting with ethyl acetate/hexanes (1:2), afforded 1.43 g of the title compound.

EXAMPLE 1

5-Chloro-1H-indole-2-carboxylic acid-[1-benzyl-3-(1,1-dioxo-hexahydro-1-thiopyran-2-yl)-2-hydroxy-3-oxo-propyl]-amide n-Butyl lithium (2 mL, 2.5 M in hexanes) was added dropwise to a solution of diisopropylamine in THF (5 mL) at 0° C. The reaction mixture was cooled to −78° C., a THF solution of tetrahydro-1,1-dioxide-2H-thiopyran (0.67 g, 5 mmol) was added dropwise, and then the mixture was warmed to 0° C. To the resulting slurry was added 5-chloro-1H-indole-2-carboxylic acid-[1-benzyl-2-methoxy-2-(hydroxymethyl-carbamoyl)-ethyl]-amide (PCT International Application Publication No. WO 96/39385) (0.42 g, 1 mmol) in 5 mL of THF and the reaction mixture was stirred for 30 min. The reaction mixture was quenched by the addition of a saturated aqueous ammonium chloride solution and extracted with ethyl acetate. The extracts were dried over magnesium sulfate, filtered, and the solvent removed in vacuo to afford 33 mg of the title compound. LC/MS (E+1) 490

The following compounds of formula (I) were prepared in a manner analogous to that described in Example 1:

5-chloro-1H-indole-2-carboxylic acid-(1-benzyl-3-(1,1-dioxo-tetrahydro-1-thiophen-2-yl)-2-hydroxy-3-oxo-propyl]-amide—LC/MS (E+1) 476;

5-chloro-1H-indole-2-carboxylic acid-(1-benzyl-3-(1,1-dioxo-1-tetrahydro-1-thiophen-2-yl)-2-methoxy-3-oxo-propyl]-amide—LC/MS (E+1) 490;

5-chloro-1H-indole-2-carboxylic acid-[1-benzyl-3-(1,1-dioxo-1-thietan-2-yl)-2-hydroxy-3-oxo-propyl]-amide—LC/MS (E+1) 462;

5-chloro-1H-indole-2-carboxylic acid-[1-benzyl-3-(1,1-dioxo-hexahydro-1-thiopyran-2-yl)-2-methoxy-3-oxo-propyl]-amide—LC/MS (E+1) 504;

5-chloro-1H-indole-2-carboxylic acid-[1-benzyl-3-(1,1-dioxo-1-thietan-2-yl)-2-methoxy-3-oxo-propyl]-amide—LC/MS (E+1) 476;

2-chloro-6H-thieno[2,3-b]pyrrole-5-carboxylic acid-[1-benzyl-3-(1,1-dioxo-tetrahydro-1-thiophen-2-yl)-2-hydroxy-3-oxo-propyl]-amide—LC/MS (E+1) 482;

2-chloro-6H-thieno[2,3-b]pyrrole-5-carboxylic acid-[1-benzyl-3-(1,1-dioxo-tetrahydro-1-thiophen-2-yl)-2-methoxy-3-oxo-propyl]-amide—LC/MS (E+1) 496;

2-chloro-6H-thieno[2,3-b]pyrrole-5-carboxylic acid-[1-benzyl-3-(1,1-dioxo-hexahydro-1-thiopyran-2-yl)-2-methoxy-3-oxo-propyl]-amide—LC/MS (E+1) 510; and 2-chloro-6H-thieno[2,3-b]pyrrole-5-carboxylic acid-[1-benzyl-3-(1,1-dioxo-1-thietan-2-yl)-2-methoxy-3-oxo-propyl]-amide—LC/MS (E+1) 482.

EXAMPLE 2

5-Chloro-1H-indole-2-carboxylic acid (1-benzyl-4-ethanesulfonyl-2-hydroxy-3-oxo-butyl)-amide A solution of methanesulfonyl-ethane (1.08 gms; 10 mmol) in 5 mL of THF was added dropwise to a 1 M lithium diisopropylamide (LDA) solution in 10 mL of THF at −78° C. The solution was then warmed to 0° C. To the resulting slurry was added a solution of 5-chloro-1H-indole-2-carboxylic acid {1-[hydroxy-(methoxy-methyl-carbamoyl)-methyl]-2-phenyl-ethyl}-amide (0.42 gms; 1 mmol) in 5 mL of THF and the reaction mixture stirred for 30 min. The reaction mixture was poured into an ice-cold mixture of ethyl acetate (50 mL)/1 N HCl (50 mL). The organic layer was separated, dried, and the solvent removed in vacuo to yield 552 mg of a foam. Further purification over a C-8 HPLC column (water, formic acid, acetonitrile) afforded 255 mg of the title product. (LC/MS ES$^+$463)

The following compounds of formula (I) were prepared in a manner analogous to that described in Example 2:

5-chloro-1H-indole-2-carboxylic acid-(1-benzyl-2-hydroxy-4-methanesulfonyl-3-oxo-butyl)-amide—LC/MS (E+1) 449; and 5-chloro-1H-indole-2-carboxylic acid-[1-benzyl-2-hydroxy-3-oxo-4-(propane-2-sulfonyl)-butyl]-amide LC/MS (E+1) 477.

Biological Protocols

The utility of the compounds of formula (I), the prodrugs thereof, and the pharmaceutically acceptable salts of the compounds and prodrugs, in the treatment or prevention of diseases (such as are detailed herein) in animals, particularly mammals (e.g., humans) may be demonstrated by the activity thereof in conventional assays known to one of ordinary skill in the relevant art, including the in vitro and in vivo assays described below. Such assays also provide a means whereby the activities of the compounds of formula (I) can be compared with the activities of other known compounds.

Glycogen Phosphorylase Production and Assays

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained according to the following procedures.

Expression and Fermentation

The HLGP cDNAs (obtained as described in Newgard, et al., Proc. Natl. Acad. Sci., 83, 8132–8136 (1986), and Newgard, et al., Proc. Natl. Acad. Sci., 263, 3850–3857 (1988), respectively) and HMGP cDNAs (obtained by screening a Stratagene (Stratagene Cloning Systems, La Jolla, Calif.) human muscle cDNA library with a polymerase chain reaction (PCR)-generated cDNA fragment based on information and methodology reported for isolation of the human skeletal muscle glycogen phosphorylase gene and partial cDNA sequence by Kubisch, et al., Center for Molecular Neurobiology, University of Hamburg, Martinistrasse 85, Hamburg, 20246 Germany; Genbank (National Center for Biotechnology Information, National Institutes of Health, USA) Accession Numbers U94774, U94775, U94776 and U94777, submitted Mar. 20, 1997; Burke, et al., Proteins, 2, 177–187 (1987); and Hwang et al., Eur. J. Biochem., 152, 267–274 (1985)) are expressed from plasmid pKK233-2 (Pharmacia Biotech. Inc., Piscataway, N.J.) in E. coli strain XL-1 Blue (Stratagene Cloning Systems, LaJolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/l pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at –70° C. until needed for purification.

The HBGP cDNA can be expressed by several methodologies, for example, by the method described by Crerar, et al., J. Biol. Chem. 270, 13748–13756 (1995), wherein the method for the expression of HBGP is as follows: the HBGP cDNA can be expressed from plasmid pTACTAC in E. coli strain 25A6. The strain is inoculated into LB medium (consisting of 10 g tryptone, 5 g yeast extract, 5 g NaCl, and 1 ml 1N NaOH per liter) plus 50 mg/L ampicillin and grown overnight, then resuspended in fresh LB medium plus 50 mg/L ampicillin, and reinoculated into a 40× volume of LB/ampicillin media containing 250 μM isopropyl-1-thio-β-D-galactoside (IPTG), 0.5 mM pyridoxine and 3 mM $MnCl_2$ and grown at 22° C. for 48–50 hours. The cells can then be harvested by centrifugation and cell pellets are frozen at –70° C. until needed for purification.

Alternatively, the HLGP and HBGP cDNAs are expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium (Sf-900 II serum free medium, Gibco BRL, Life Technologies, Grand Island, N.Y.) are infected at an moi of 0.5 and at a cell density of $2 \times 10^6$ cells/ml. After growth for 72 hours at 27° C., cells are centrifuged, and the cell pellets frozen at –70° C. until needed for purification.

Purification of Glycogen Phoshorylase Expressed in E. coli

The E. coli cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 μg/ml | Pepstatin A |
| 0.5 μg/ml | Leupeptin |
| 0.2 mM | phenylmethylsulfonyl fluoride (PMSF), and |
| 0.5 mM | EDTA, | lysed by pretreatment with 200 μg/ml lysozyme and 3 μg/ml DNAase followed by sonication in 250 ml batches for 5×1.5 minutes on ice using a Branson Model 450 ultrasonic cell disrupter (Branson Sonic Power Co., Danbury Conn.). The E. coli cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong, et al., Journal of Chromatography, 584, 77–84 (1992). Five hundred ml of the filtered soluble fraction of cell lysates (prepared from approximately 160–250 g of original cell pellet) are loaded onto a 130 ml column of IMAC Chelating-Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 (equilibration buffer). The column is washed with equilibration buffer until the $A_{280}$ returns to baseline. The sample is then eluted from the column with the same buffer containing 100 mM imidazole to remove the bound GP and other bound proteins. Fractions containing the GP activity are pooled (approximately 600 ml), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/ml and 0.7 μg/ml concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice and subjected to a second chromatographic step (below) if necessary.

5'-AMP-Sepharose Chromatography

The desalted pooled GP sample (approximately 600 mL) is then mixed with 70 ml of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the $A_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme activity described below and visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl2, plus the following protease inhibitors:

| | |
|---|---|
| 0.7 μg/ml | Pepstatin A |
| 0.5 μg/ml | Leupeptin |
| 0.2 mM | phenylmethylsulfonyl fluoride (PMSF), and |
| 0.5 mM | EDTA, | lysed by pretreatment with 3 μg/ml DNAase followed by sonication in batches for 3×1 minutes on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, as described below, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 μg/ml leupeptin and 1.0 μg/ml pepstatin A. The fraction is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM N,N-bis-(2-hydroxyethyl)-2-aminoethanesulfonic acid (BES), 1.0 mM DTT, 0.5 mM EDTA, 5 mM NaCl, pH 6.8 buffer and stored on ice until use.

Determination of GP Enzyme Activity

A) Activation of GP: Conversion of GPb to GPa

Prior to the determination of GP enzyme activity, the enzyme is converted from the inactive form as expressed in *E. coli* strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the follow procedure.

GP Reaction with Immobilized Phosphorylase Kinase

Phosphorylase kinase (Sigma Chemical Company, St. Louis, Mo.) is immobilized on Affi-Gel® 10 (BioRad Corp., Melville, N.Y.) in accordance with the manufacturer's instructions. In brief, the phosphorylase kinase enzyme (10 mg) is incubated with washed Affi-Gel® beads (1 ml) in 2.5 ml of 100 mM HEPES and 80 mM $CaCl_2$ at pH 7.4 for 4 hours at 4° C. The Affi-Gel® beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel® immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive GPb obtained from 5'-AMP-Sepharose chromatography above (from *E. coli*) or the mixture of GPa and GPb obtained from IMAC above (from Sf9 cells) is diluted 1:10 with the kinase assay buffer then mixed with the aforementioned phosphorylase kinase enzyme immobilized on the Affi-Gel® beads. NaATP is added to 5 mM and $MgCl_2$ to 6 mM. The resulting mixture is mixed gently at 25° C. for 30 to 60 minutes. The activated sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total HLGPa} = \frac{\text{HLGP activity} - \text{AMP}}{\text{HLGP activity} + \text{AMP}}$$

Alternately, the conversion of GPb to GPa can be monitored by isoelectric focusing, based on the shift in electrophoretic mobility noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) according to the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to *E. coli* derived GPa and GPb standards run in parallel on the same gels as the experimental samples.

B) GPa Activity Assay

The disease/condition treating/preventing activities described herein of the compounds of formula (I) can be indirectly determined by assessing the effect of the compounds of formula (I) on the activity of the activated form of glycogen phosphorylase (GPa) by one of two methods: (1) GPa activity is measured in the forward direction by monitoring the production of glucose-1-phosphate from glycogen, or (2) by following the reverse reaction, measuring glycogen synthesis from glucose-1-phosphate by the release of inorganic phosphate. All reactions are run in triplicate in 96-well microtiter plates, and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al., Clinical Chemistry 23, 1711–1717 (1977) modified as follows: 1 to 100 μg GPa, 10 units phosphoglucomutase and 15 units glucose-6-phosphate dehydrogenase (Boehringer Mannheim Biochemicals, Indianapolis, Ind.) are diluted to 1 mL in Buffer D (pH 7.2, 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol). Twenty μl of this stock is added to 80 μl of Buffer D containing 0.47 mg/mL glycogen, 9.4 mM glucose, 0.63 mM of the oxidized form of nicotinamide adenine dinucleotide phosphate (NADP+). The formula (I) compound to be tested is added as 5 μl, of solution in 14% dimethylsulfoxide (DMSO) prior to the addition of the enzymes. The basal rate of GPa enzyme activity in the absence of inhibitors, e.g., a compound of formula (I), is determined by adding 5 μl, of 14% DMSO and a fully-inhibited rate of GPa enzyme activity is obtained by adding 20 μl, of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers, et al., Can. J. Biochem., 48, 746–754 (1970) modified as follows: 1 to 100 μg GPa is diluted to 1 ml in Buffer E (pH 7.2, 50 mM HEPES, 100 mM KCl, 2.5 mM EGTA, 2.5 mM $MgCl_2$ and 0.5 mM dithiothreitol). Twenty μl of this stock is added to 80 μl of Buffer E with 1.25 mg/ml glycogen, 9.4 mM glucose, and 0.63 mM glucose-1-phosphate. The formula (I) compound to be tested is added as 5 μl of solution in 14% DMSO prior to the addition of the enzyme. The basal rate of GPa enzyme activity in the absence of added inhibitors, e.g., a compound of formula (I), is determined by adding 5 μl of 14% DMSO and a fully-inhibited rate of GPa enzyme activity is obtained by adding 20 μL of 50 mM caffeine. This mixture is incubated at room temperature for 1 hour and the inorganic phosphate released from the glucose-1-phosphate is measured by the general method of Lanzetta et al., Anal. Biochem., 100, 95–97 (1979)] modified as follows: 150 μl of 10 mg/ml ammonium molybdate, 0.38 mg/ml malachite green in 1 N HCl is added to 100 μl of the enzyme mix. After a 20 minute incubation at room temperature, the absorbance is measured at 620 nm.

The above assays, carried out with a range of concentrations of formula (I) compounds, allows the determination of an $IC_{50}$ value (concentration of a compound required for 50% inhibition) for the in vitro inhibition of GPa enzyme activity by that compound.

The compounds of formula (I) are readily adapted to clinical use as hypoglycemic agents. The hypoglycemic activity of the compounds of formula (I) can be determined by the amount of a formula (I) compound that reduces glucose levels relative to a vehicle without a formula (I) compound in male ob/ob mice. The test also allows the determination of an approximate minimal effective dose (MED) value for the in vivo reduction of plasma glucose concentration in such mice for such formula (I) compounds.

Since the concentration of glucose in blood is closely related to the development of diabetic disorders, the compounds of formula (I), by virtue of their hypoglycemic action, prevent, arrest and/or regress diabetic disorders.

Five to eight week old male C57BL/6J-ob/ob mice (Jackson Laboratory, Bar Harbor, Me.) are housed five per cage under standard animal care practices. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for metabolite analysis. Animals are assigned to treatment groups so that each group has a similar mean for plasma glucose concentration. After group assignment, animals are dosed orally each day for four days with the vehicle consisting of either: (1) 0.25% w/v methyl cellulose in water without pH adjustment; or (2) 0.1% Pluronic® P105 Block Copolymer Surfactant (BASF Corporation, Parsippany, N.J.) in 0.1% saline without pH adjustment. On day 5, the animals are weighed again and then dosed orally with a formula (I) compound, or the vehicle alone. All compounds are administered in vehicle consisting of either: (1) 0.25% w/v methyl cellulose in water; (2) 10% DMSO/0.1% Pluronic® in 0.1% saline without pH adjustment; or 3) neat PEG 400 without pH adjustment. The animals are then bled from the retro-orbital sinus three hours later for determination of blood metabolite levels. The freshly collected samples are centrifuged for two minutes at 10,000×g at room temperature. The supernatant is analyzed for glucose, for example, by the Abbott VP™ (Abbott Laboratories, Diagnostics Division, Irving, Tex.) and VP Super System® Autoanalyzer (Abbott Laboratories, Irving, Tex.), or by the Abbott Spectrum CCX™ (Abbott Laboratories, Irving, Tex.) using the A-Gent™Glucose-UV Test reagent system (Abbott Laboratories, Irving, Tex.) (a modification of the method of Richterich and Dauwalder, Schweizerische Medizinische Wochenschrift, 101, 860 (1971)) (hexokinase method) using a 100 mg/dl standard. Plasma glucose is then calculated using the following equation:

Plasma glucose (mg/dl)=Sample value×8.14 where 8.14 is the dilution factor, adjusted for plasma hematocrit (assuming the hematocrit is 44%).

The animals dosed with vehicle maintain substantially unchanged hyperglycemic glucose levels (e.g., greater than or equal to 250 mg/dl), animals treated with compounds having hypoglycemic activity at suitable doses have significantly depressed glucose levels. Hypoglycemic activity of the compounds of formula (I) is determined by statistical analysis (unpaired t-test) of the mean plasma glucose concentration between the test compound group and vehicle-treated group on day 5. The above assay carried out with a range of doses of a formula (I) compound allows the determination of an approximate minimal effective dose (MED) value for the in vivo reduction of plasma glucose concentration.

The compounds of formula (I) are readily adapted to clinical use as hyperinsulinemia reversing agents, triglyceride lowering agents and hypocholesterolemic agents. Such activity can be determined by the amount of the compound of formula (I) that reduces insulin, triglycerides or cholesterol levels relative to a control vehicle without test compound in male ob/ob mice.

Since the concentration of cholesterol in blood is closely related to the development of cardiovascular, cerebral vascular or peripheral vascular disorders, the compounds of formula (I), by virtue of their hypocholesterolemic action, prevent, arrest and/or regress atherosclerosis.

Since the concentration of insulin in blood is related to the promotion of vascular cell growth and increased renal sodium retention, (in addition to the other actions, e.g., promotion of glucose utilization) and these functions are known causes of hypertension, the compounds of formula (I), by virtue of their hypoinsulinemic action, prevent, arrest and/or regress hypertension.

Since the concentration of triglycerides in blood contributes to the overall levels of blood lipids, the compounds of formula (I), by virtue of their triglyceride lowering and/or free fatty acid lowering activity prevent, arrest and/or regress hyperlipidemia.

Five to eight week old male C57BU6J-ob/ob mice (Jackson Laboratory, Bar Harbor, Me.) are housed five per cage under standard animal care practices and fed standard rodent diet ad libitum. After a one-week acclimation period, the animals are weighed and 25 microliters of blood are collected from the retro-orbital sinus prior to any treatment. The blood sample is immediately diluted 1:5 with saline containing 0.025% sodium heparin, and held on ice for plasma glucose analysis. Animals are assigned to treatment groups so that each group has a similar mean for plasma glucose concentration. The compound of formula (I) to be tested is administered by oral gavage as an approximately 0.02% to 2.0% solution (w/v) in either: (1) 10% DMSO/0.1% Pluronic® P105 Block Copolymer Surfactant (BASF Corporation, Parsippany, N.J.) in 0.1% saline without pH adjustment, or (2) 0.25% w/v methylcellulose in water without pH adjustment. Alternatively, the compound of formula (I) may be dissolved or suspended in neat PEG 400, and administered by oral gavage. Single daily dosing (s.i.d.), twice daily dosing (b.i.d.), or thrice daily dosing (t.i.d.) is maintained, for example, 1 to 28 days. Control mice receive the 10% DMSO/0.1% Pluronice P105 in 0.1% saline without pH adjustment, or the 0.25% w/v methylcellulose in water without pH adjustment, or the neat PEG 400 without pH adjustment.

One to three hours after the last dose is administered, the animals are sacrificed by decapitation and trunk blood is collected in 0.5 ml serum separator tubes containing 3.6 mg of a 1:1 weight/weight sodium fluoride:potassium oxalate mixture. The freshly collected samples are centrifuged for two minutes at 10,000×g at room temperature, and the serum supernatant is transferred and diluted 1:1 volume/volume with a 1TIU/ml aprotinin solution in 0.1% saline without pH adjustment.

The diluted serum samples are then stored at −80° C. until analysis. The thawed, diluted serum samples are analyzed for insulin, triglycerides, free fatty acids and cholesterol levels. Serum insulin concentration is determined using Equate® RIA INSULIN kits (double antibody method; as specified by the manufacturer) available from Binax, South Portland, Me. The inter assay coefficient of variation is ≦10%. Serum triglycerides are determined using the Abbott VP™ and VP Super System® Autoanalyzer (Abbott Laboratories, Irving, Tex.), or the Abbott Spectrum CCX™ (Abbott Laboratories, Irving, Tex.) using the A-Gent™ Triglycerides Test reagent system (Abbott Laboratories, Diagnostics Division, Irving, Tex.) (lipase-coupled enzyme method; a modification of the method of Sampson, et al., Clinical Chemistry, 21, 1983 (1975)). Serum or plasma total cholesterol levels are determined using the Abbott VP™ and VP Super System® Autoanalyzer (Abbott Laboratories, Irving, Tex.), and A-Gent™ Cholesterol Test reagent system (cholesterol esterase-coupled enzyme method; a modification of the method of Allain, et al., Clinical Chemistry, 20, 470 (1974)) using 100 and 300 mg/dl standards. Serum or plasma free fatty acid concentration is determined utilizing a kit from Amano International Enzyme Co., Inc., as adapted for use with the Abbott VP™ and VP Super System® Autoanalyzer (Abbott Laboratories, Irving, Tex.), or the Abbott Spectrum CCX™ (Abbott Laboratories, Irving, Tex.). Serum or plasma insulin, triglycerides, free fatty acids, and total cholesterol levels are then calculated using the following equations:

Serum or plasma insulin ($\mu$U/ml)=Sample value×2

Serum or plasma triglycerides (mg/dl)=Sample value×2

Serum or plasma total cholesterol (mg/dl)=Sample value×2

Serum or plasma free fatty acid ($\mu$Eq/l)=Sample value×2 where 2 is the dilution factor.

The animals dosed with vehicle maintain substantially unchanged, elevated serum or plasma insulin (e.g., 275 $\mu$U/ml), serum or plasma triglycerides (e.g., 235 mg/dl), serum or plasma free fatty acid (1500 mEq/ml) and serum or plasma total cholesterol (e.g., 190 mg/dl) levels, while animals treated with compounds of formula (I) generally display reduced serum or plasma insulin, triglycerides, free fatty acid, and total cholesterol levels. The serum or plasma insulin, triglycerides, free fatty acid, and total cholesterol lowering activity of the compounds of formula (I) are determined by statistical analysis (unpaired t-test) of the mean serum or plasma insulin, triglycerides, or total cholesterol concentration between the formula (I) compound group and the vehicle-treated control group.

What is claimed is:

1. A compound of formula (I)

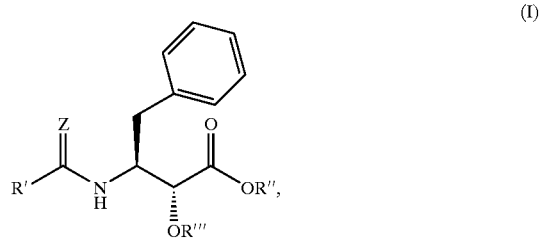

and the pharmaceutically acceptable salts of said compounds, wherein:

R' is

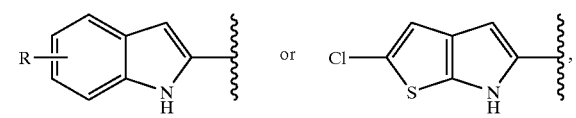

wherein R represents from 1–3 substituents independently selected from the group consisting of hydrogen; amino; cyano; nitro; halogen; —($C_1$–$C_6$)alkyl; and —($C_1$–$C_6$)alkoxy, wherein said —($C_1$–$C_6$)alkyl group and said —($C_1$–$C_6$)alkoxy group are each optionally substituted with from 1–6 fluorine atoms;

R'' is

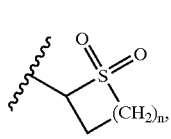

(i)

wherein n represents an integer from 1–3; or (ii) —CHR$^a$SO$_2$(C$_1$–C$_6$)alkyl, wherein R$^a$ is hydrogen or —(C$_1$–C$_6$)alkyl;

R''' is hydrogen or —(C$_1$–C$_6$)alkyl; and

Z is oxygen or sulfur.

2. A compound of claim 1, wherein:

R' is

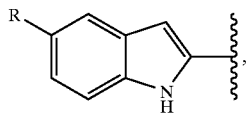

wherein R is selected from the group consisting of chloro, fluoro, and methyl;

R'' is

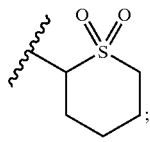

R''' is hydrogen or methyl; and

Z is oxygen.

3. A compound of claim 1, wherein:

R' is

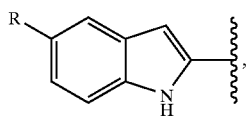

wherein R is selected from the group consisting of chloro, fluoro, and methyl;

R'' is

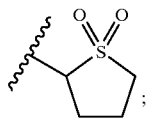

R''' is hydrogen or methyl; and

Z is oxygen.

4. A compound of claim 1, wherein:

R' is

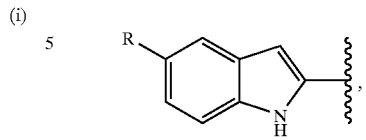

wherein R is selected from the group consisting of chloro, fluoro, and methyl;

R'' is

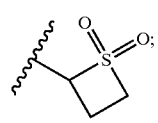

R''' is hydrogen; and

Z is oxygen.

5. A compound of claim 1 selected from the group consisting of:

5-chloro-1H-indole-2-carboxylic acid-(1-benzyl-3-(1,1-dioxo-tetrahydro-1-thiophen-2-yl)-2-hydroxy-3-oxo-propyl]-amide;

5-chloro-1H-indole-2-carboxylic acid-(1-benzyl-3-(1,1-dioxo-1-tetrahydro-1-thiophen-2-yl)-2-methoxy-3-oxo-propyl]-amide;

5-chloro-1H-indole-2-carboxylic acid-[1-benzyl-3-(1,1-dioxo-hexahydro-1-thiopyran-2-yl)-2-methoxy-3-oxo-propyl]-amide; and 5-chloro-1H-indole-2-carboxylic acid-[1-benzyl-3-(1,1-dioxo-hexahydro-1-thiopyran-2-yl)-2-hydroxy-3-oxo-propyl]-amide; and the pharmaceutically acceptable salts of the compounds.

6. A compound of claim 1, wherein

R' is

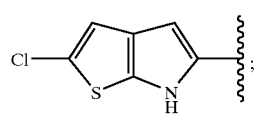

R'' is

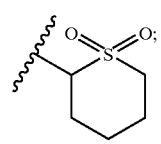

R''' is methyl; and

Z is oxygen.

7. A compound of claim 1, wherein:

R' is

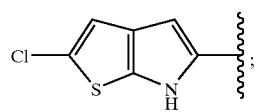

R″ is

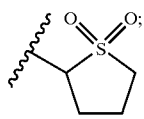

R‴ is hydrogen or methyl; and

Z is oxygen.

8. A compound of claim 1 selected from the group consisting of:
2-chloro-6H-thieno[2,3-b]pyrrole-5-carboxylic acid-[1-benzyl-3-(1,1-dioxo-tetrahydro-1-thiophen-2-yl)-2-hydroxy-3-oxo-propyl]-amide;
2-chloro-6H-thieno[2,3-b]pyrrole-5-carboxylic acid-[1-benzyl-3-(1,1-dioxo-tetrahydro-1-thiophen-2-yl)-2-methoxy-3-oxo-propyl]-amide; and
2-chloro-6H-thieno[2,3-b]pyrrole-5-carboxylic acid-[1-benzyl-3-(1,1-dioxo-hexahydro-1-thiopyran-2-yl)-2-methoxy-3-oxo-propyl]-amide; and the pharmaceutically acceptable salts of said compounds.

9. A pharmaceutical composition comprising a compound of claim 1, or a pharmaceutically acceptable salt of said compound and a pharmaceutically acceptable carrier, vehicle, or diluent.

10. A method of treating a condition selected from the group consisting of diabetes, insulin resistance, diabetic neuropathy, diabetic nephropathy, and diabetic retinopathy, hypertriglyceridemia, hyperlipidemia, hyperglycemia, hypertension, tissue ischemia, and which comprises administering to a mammal in need of such treatment, a therapeutically effective amount of a compound of claim 1, or a pharmaceutically acceptable salt of said compound or a pharmaceutical composition comprising said compound of claim 1, thereof, or said pharmaceutically acceptable salt of said compound and a pharmaceutically acceptable carrier, vehicle, or diluent.

11. A method of claim 10 wherein said condition is diabetes.

* * * * *